(12) United States Patent
Frid

(10) Patent No.: US 7,396,363 B2
(45) Date of Patent: Jul. 8, 2008

(54) HEMODYNAMIC LUMINAL ENDOPROSTHESIS

(75) Inventor: Noureddine Frid, Beersel (BE)

(73) Assignee: F.R.I.D. R&D Benelux, Mons (BE)

( * ) Notice: Subject to any disclaimer, the term of this patent is extended or adjusted under 35 U.S.C. 154(b) by 115 days.

(21) Appl. No.: 10/518,860

(22) PCT Filed: Jun. 17, 2003

(86) PCT No.: PCT/EP03/50231

§ 371 (c)(1),
(2), (4) Date: Dec. 17, 2003

(87) PCT Pub. No.: WO03/105728

PCT Pub. Date: Dec. 24, 2003

(65) Prior Publication Data

US 2005/0288770 A1    Dec. 29, 2005

(30) Foreign Application Priority Data

Jun. 18, 2002    (EP) .................................. 02100720

(51) Int. Cl.
*A61F 2/06* (2006.01)

(52) U.S. Cl. .................... 623/1.15; 623/1.27; 623/1.53

(58) Field of Classification Search ................ 623/1.15, 623/1.16, 1.53, 1.27, 1.35; 87/9
See application file for complete search history.

(56) References Cited

U.S. PATENT DOCUMENTS

| | | | | |
|---|---|---|---|---|
| 1,104,778 A * | 7/1914 | Cobb | ............................... | 87/9 |
| 3,334,629 A * | 8/1967 | Cohn | .......................... | 606/194 |
| 4,416,028 A * | 11/1983 | Eriksson et al. | ............. | 623/1.38 |
| 4,787,901 A * | 11/1988 | Baykut | ....................... | 623/1.26 |
| 5,197,976 A * | 3/1993 | Herweck et al. | ........... | 623/1.27 |
| 5,287,790 A * | 2/1994 | Akiyama et al. | .................. | 87/9 |
| 5,383,925 A * | 1/1995 | Schmitt | ..................... | 623/1.53 |
| 5,685,865 A * | 11/1997 | Cosgrove et al. | ............ | 604/239 |
| 5,709,713 A * | 1/1998 | Evans et al. | ................. | 623/1.53 |
| 5,718,159 A * | 2/1998 | Thompson | ...................... | 87/33 |
| 5,741,332 A * | 4/1998 | Schmitt | .................... | 623/23.64 |
| 5,906,641 A * | 5/1999 | Thompson et al. | .......... | 623/1.15 |
| 6,149,682 A * | 11/2000 | Frid | .......................... | 623/1.35 |
| 6,306,164 B1 * | 10/2001 | Kujawski | .................... | 623/1.35 |
| 6,325,882 B1 * | 12/2001 | Schroeder | .................... | 156/228 |
| 6,348,066 B1 | 2/2002 | Pinchuk et al. | | |
| 6,398,807 B1 * | 6/2002 | Chouinard et al. | ......... | 623/1.35 |
| 6,641,605 B1 * | 11/2003 | Stergiopulos | ................ | 623/1.1 |
| 6,645,242 B1 * | 11/2003 | Quinn | ........................ | 623/1.16 |
| 6,926,735 B2 * | 8/2005 | Henderson | ................. | 623/1.42 |

FOREIGN PATENT DOCUMENTS

| | | | |
|---|---|---|---|
| EP | 0861638 A2 * | 9/1998 | |
| EP | 1153581 A | 11/2001 | |
| EP | 1234554 A | 8/2002 | |
| WO | WO-9858599 A * | 12/1998 | |
| WO | WO 01/01887 A | 1/2001 | |

* cited by examiner

*Primary Examiner*—Paul B. Prebilic
(74) *Attorney, Agent, or Firm*—Townsend and Townsend and Crew LLP

(57) ABSTRACT

A multilayer braided luminal self-expanding stent (4) for an anatomical conduit (8) comprising a outer braided peripheral stent (10) which is permanently linked to an inner, braided, hemodynamic flow deflector (2) by at least a pair of filaments (12) that make part of a common braided structure.

2 Claims, 2 Drawing Sheets

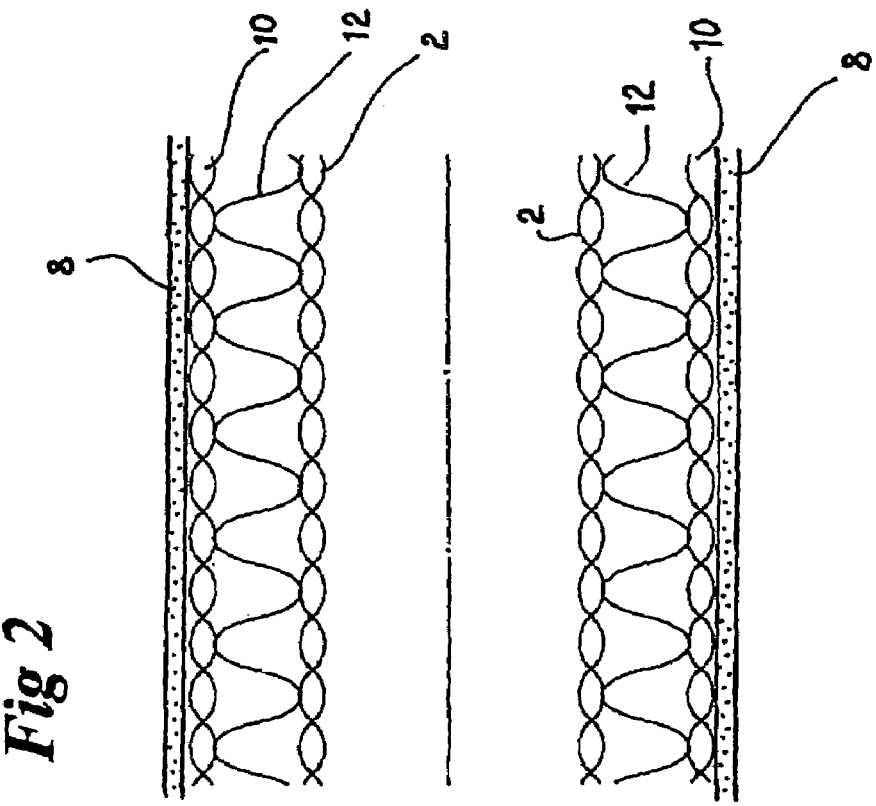
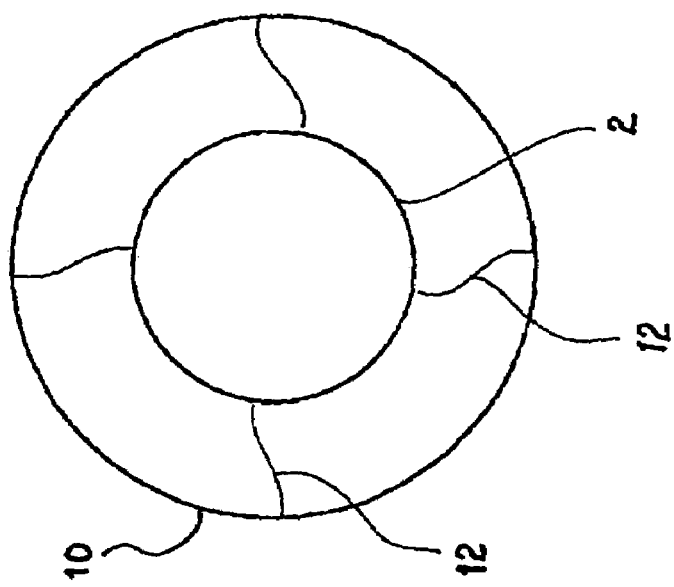

HEMODYNAMIC LUMINAL ENDOPROSTHESIS

The invention concerns luminal endoprostheses to be placed in blood vessels, such as stents.

BACKGROUND OF THE INVENTION

Stents are generally placed within the lumen of a narrowed artery in cases when the outcome of angioplasty is uncertain, e.g. in the case of stenoses, recanalized occlusions or vessel dissection.

When a stent is unfolded, it applies a constant outward force on the vessel, maintaining the desired dimensions of the lumen and thus reducing the effects of stenosis.

However, recent studies on the subject prevealed that placement of a luminal endoprosthesis can cause injuries to the artery wall, which leads to what is called intimal hyperplasia.

The vascular wall is composed of three layers, namely the intima (innermost layer composed of a single layer of endothelial cells), the media (middle layer which is composed of smooth muscle cells, elastic sheets, elastic fibrils network and bundles of collagenous fibers) and the advantitia (the outer layer).

It is now well established that intimal hyperplasia is the main process that induces belated narrowing of the lumen, even one or two years after intervention. It is related to the loss of endothelium and to medial injuries, which lead to an accelerated luminal smooth muscles proliferation migrating from the media or the intima and later to atherosclerosis degeneration.

Presently, studies to reduce what is called intimal hyperplasia (small muscle tissue proliferation which leads to restenosis) are aimed at anti-proliferation or anti-mitotic drugs that are fixed on the stent surface via a polymer matrix.

These methods suffer from several difficulties:
the non uniformity of polymer surface and consequently the lack of consistency of the local drug delivery.
the lack of consistency of the kinetic degradation of the polymer matrix.
the stability of the polymer fixation on the surface of the stent.
the determination of the right value of the drug dose to be affixed on the matrix.

The drugs used are similar to those which are used as anti-cancer drugs, e.g. Taxol and Rapamycin. The use of high amounts of these molecules could be very harmful for the patient.

The restenosis of the stent induced by intimal hyperplasia poses a major problem for stent efficiency, mainly for arteries such as femorals, internal carotids or coronaries.

For the femoral artery, for example, many clinical trials show that stents give poor results due to the restenosis which is a consequence of intimal hyperplasia; 50 to 60% failure.

A new approach showed that the restenosis was bound to unexpected mechanical problems.

Femoral Artery:

A low shear stress along the cell wall is considered as an important factor of atherosclerotic plaque formation. It has been correlated with intimal thickening and has been shown to alter endothelial cells structure and function.

The disturbed flow increases cell turnover particularly in the areas of low blood velocity, which could explain the loss of contact inhibition of cell growth.

Internal Carotid:

The human carotid bifurcation is another example where flow model studies have demonstrated that the intimal plaques form in the low shear stress region of the carotid sinus opposite the flow and not in the high shear stress region along the inner wall of the carotid artery.

Coronary Artery

Similarly, the low shear stress is now shown to be a main cause of plaques formation at the branch points just distal to the bifurcation of the left main coronary artery into LAD and circumflex. This region exhibits a low blood flow velocity and a low shear stress, in other words the coronary artery tree demonstrates also a relationship between the shear stress and plaque formation.

The coronary arteries are subject to two systolic phases and one diastolic flow episode during each cardiac cycle, thus potentially placing them at a higher risk rank than systemic arteries to atherosclerosis. Shear stress oscillation is directly influenced by heart rate. At higher rate, coronary arteries are exposed to more acute oscillatory than at low shear stress episodes, which accelerate the formation of atherosclerosis plaques. For example, an increase in the mean heart rate from 70 to 80 beats/min would result in an increase of over 5 million heart beats per year. The duration of the systolic phase is generally constant for varying heart rates, whereas the duration of diastolic phase shortens with increasing heart rates.

It is important to mention that the effect of heart rate on atherosclerosis is associated with carotid artery atherosclerosis.

Many stents are well known and are described in the prior art.

In WO 01/01887, it is disclosed a composite stent which comprises an inner PTFE tubular structure and an outer PTFE tubular structure assembled about the inner structure and between these two structures is interposed a distensible stent. Thus, this layered structure improves both axial and radial compliance of the stent.

The invention described in WO 02/47579 concerns a prosthesis for blood vessels whose frame comprises a plurality of interconnected layers which are formed of two interwoven frame wires. This configuration allows increasing both the stability and the strength of the stent.

However there is no document in the prior art which discloses the feature of the present invention to favour blood flow.

SUMMARY OF THE INVENTION

A higher flow velocity could suppress neointimal hyperplasia. However, this seems at first sight an absurdity, because it implies that, at constant flow rate, the section would have to be reduced. This led to the idea to design a stent in such a way that the flow velocity would remain globally the same, but would be increased along the cell wall, consequently improving the shear stress at wall level.

During the 12$^{th}$ conference of the European Society of Biomechanics (Dublin 2000) Nikos Stergiopolos demonstrated that avoiding intimal hyperplasia proliferation mainly in the case of low flow could be done by placing a streamlined cylindrical body in the centre of blood stream. The body deflects the central core of flow towards the wall, increasing the wall shear stress.

However, this brilliant theory could hardly be reduced to practice. The placing of a cylinder in the centre of the stream line of a diseased artery is not easy by itself, and it needs to be coupled with the prior placing of a standard stent, both to hold the atherosclerosis plaques and to anchor the cylinder. The inner cylinder further needs to be stable and firmly held in place.

The Applicant has developed a stent made out of a plurality of interlaced braided layers of metal filaments.

Prior experience in this field allowed him to develop a new type of stent which is braided in such a way that the making of a peripheral stent, a central deflecting cylinder and a linking between these two elements is achieved in a single shot.

The subject of the invention is a multilayer braided luminal self-expanding stent for an anatomical conduit comprising an outer braided peripheral stent structure which is permanently linked to a central hollow braided core acting as an inner braided hemodynamic flow deflector by at least two filaments said outer peripheral stent structure (10), said central hollow braided core and said at least a pair of filaments (12) make part of a common braided structure, the gap between the two commonly braided structures is broadly between 10 to 90% of the nominal diameter of the outer stent.

The multilayer technology seems to be the right solution because it is possible to have in one shot both cylinders made and simultaneously linked together.

In other words, a multilayer machine which is able to braid six layers in one shot could be used to braid the first two layers together around a mandrill with the full number of wires needed.

The second and the third layers will handle only four or eight carriers with filled wires in order to connect the first two layers to the last two ones.

The result is a self-expanding stent as described above.

The two cylindrical structures are linked together by this multilayer technique in such a way that they form one single body.

The advantage of this design is that, when put in place, it increases the velocity of the blood along the inner wall of the vessel and thereby the shear stress. An increase of shear stress of the blood elongates endothelial cells in the direction of the flow. The cells also align themselves in the direction of the flow, and the shape of a confluent layer of endothelial cells changes from polygonal to ellipsoid when exposed to unidirectional shear. Endothelial cells produce nitric oxide, which is an important element for maintaining the vasodilator or vasorelaxing tonus in blood vessels. Nitric oxide inhibits platelet aggregation and adhesion, and modulates leukocyte adhesion and migration. In other words inducing the production of nitric oxide prevents stent restenosis by eliminating intimal hyperplasia thickening.

BRIEF DESCRIPTION OF THE FIGURES

Other particulars and advantages of the invention will become apparent from the description hereinafter of some particular embodiments of the invention, reference being made to the appended drawings in which:

FIG. 2 is a sketch of a sectional view along the axis of the stent.

FIG. 3 is a sketch of a sectional view normal to the axis of the stent

DETAILED DESCRIPTION OF THE FIGURES

Figure 1:
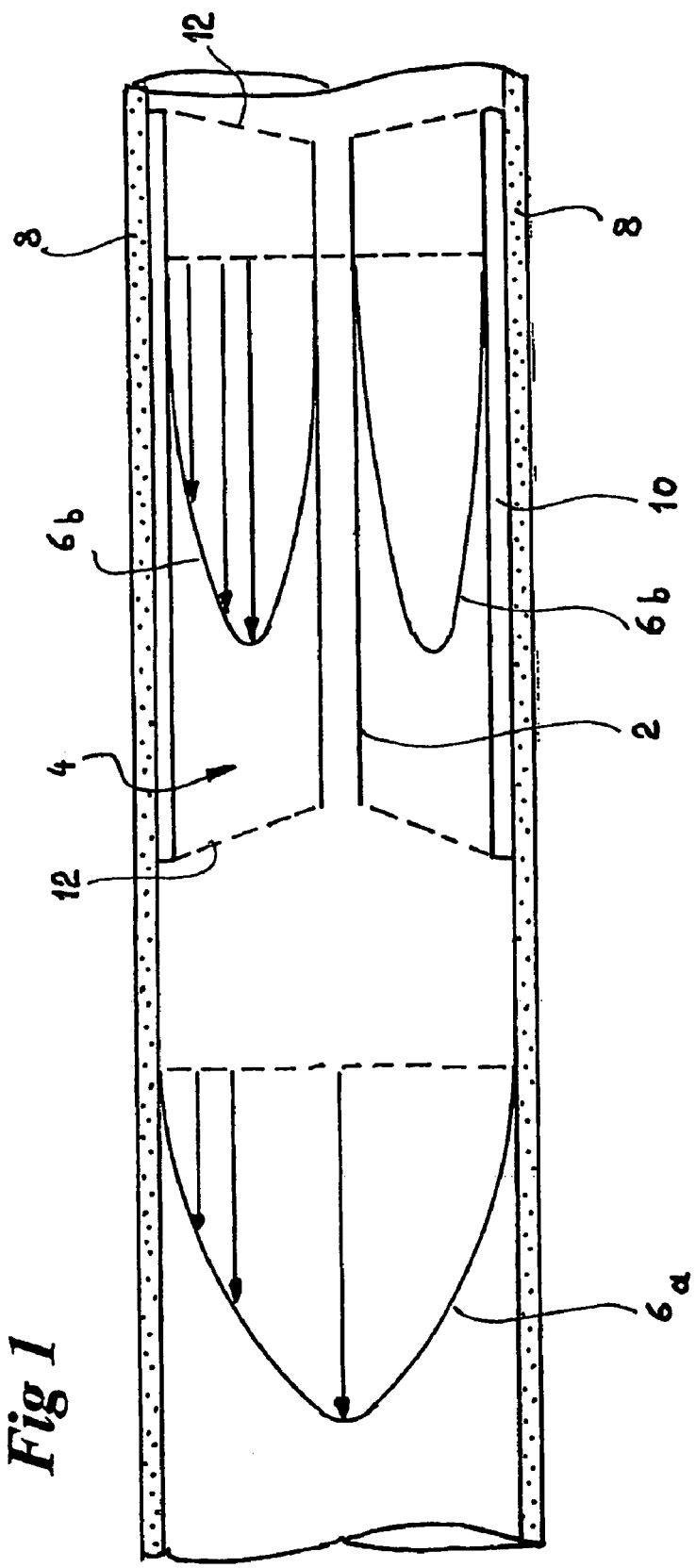
FIG. 1 is a sketch of the aspect of the blood flow, with and without the inner core of a stent according to the invention.

FIG. 1 shows a diagrammatical view of the velocity profile of a flow of blood, with (right side of the FIG. 1) or without (left side of the FIG. 1) the hemodynamic deflecting core 2 of the stent of the invention 4.

In the absence of core 2, the velocity cube 6*a* is classical: the velocity decreases progressively from a maximum to zero at the very contact of the wall 8, allowing the anarchic growth of wall cells that in time will impede the even passage of blood.

Turning now to the right side of the figure, one can see that the blood, deflected from the centre of the vessel by the hemodynamic core 2, induces a steeper flow profile 6*b* near the wall 8. The shear stress thus improved drags along the molecules that would induce a reaction of the wall cells.

FIGS. 2 and 3 display the general structure of the stent 4, that exhibits a central hollow braided hemodynamic core 2 and a "classical" peripheral stent structure 10, the core and the peripheral structures being linked by wires 12 belonging to both braids.

To obtain this kind of structure, at least one or two wires are braided in helix simultaneously with the inner and the outer layers of braiding.

To control the empty space between the two cylindrical structures, the easiest way is to fill the intermediate spindles with filaments of a material that is able to be dissolved (e.g. in hot water) after the braiding process, thus leaving a corresponding empty space in the braiding.

EXAMPLE

A braiding machine is equipped with spindles so as to be able to realise a multilayer braid made out of 24 or 48 wires, according to the nominal size of the stent.

The spindles corresponding to the first two layers are loaded with metal wires. The spindles corresponding to the $3^{rd}$ layer are loaded with PVA (polyvinylalcohol) filament (Kuralon® or Solveon®), but for two to five of them (according to the final size of the stent), that are loaded in a symmetrical way (thus in a diametrically opposed position), by metal wires. These metal wires which make the junction with the last two layers, are made out, as the first and second one, of metal.

When the braiding is finished, the braid is extracted from the mandrel on which it has been braided. It is then put in hot water (between 50 and 70° C.) so as to dissolve the PVA filaments, thus freeing the space between the two distinct—inner and outer—structures.

The thickness of the PVA filament can be varied according to the width to be preserved between the peripheral stent and the inner core 2. The dimensions of the hollow inner core 2 itself are sufficient to modify the hemodynamic conditions of the blood flow, as described above.

In vitro experiments showed that the shear stress must reach a value of 15 dyne/cm$^2$ to affect the growth of endothelial cells. Below this value, the shear stress induce the formation of plaque and an anarchic growth of muscular cells. Below 2 dyne/cm$^2$, the neointimal formation increases sharply, provoking rapid lesions.

The framework of the present stent can be made out of nickel titanium alloy or in cobalt alloy as Elgiloy or Phynox, or in stainless steel.

The metal wires can be submitted to a thermal treatment so as to reach a rigidity sufficient to withstand the crushing.

A further advantage of the present structure is that it reacts as a single element, capable of being squeezed and to elongate exactly as a classical stent. The structure is also very light, it can be reduced to a minute diameter, allowing an easy placement and a very good flexibility. It is further possible to use classical applicators to put it in place in a single operation.

The invention claimed is:

1. A multilayer luminal braided self-expanding stent for an anatomical conduit, expandable from a reduced diameter to a nominal diameter, comprising a cylindrical outer braided peripheral stent structure comprising a layer wherein
said outer peripheral stent structure is permanently linked by at least a pair of filaments to a cylindrical central hollow braided core comprising a layer capable of acting as an inner braided hemodynamic flow deflector;
said outer peripheral stent structure, said central hollow braided core and said at least a pair of filaments constitute a commonly braided metal structure, a gap of between 10 to 90% of the nominal diameter of the outer stent structure extends between the central braided core and the outer stent structure of the commonly braided structure, wherein said outer peripheral stent structure and said central braided core of the commonly braided structure are permanently linked and extend parallel to each other along their respective full lengths.

2. A multilayer stent according to claim 1 wherein the outer braided peripheral stent structure comprises two layers which are connected by at least a pair of filaments in order to connect the two layers to the deflector, the latter comprising at least two layers.

* * * * *